United States Patent [19]

Eder et al.

[11] Patent Number: 4,719,605

[45] Date of Patent: Jan. 12, 1988

[54] SELF-CALIBRATING ULTRASONIC RANGE FINDER

[75] Inventors: Kenneth C. Eder, New Brighton, Minn.; Christos M. Koukovinis, Freeport, Ill.

[73] Assignee: Honeywell Inc., Minneapolis, Minn.

[21] Appl. No.: 681,175

[22] Filed: Dec. 13, 1984

[51] Int. Cl.⁴ .......................... G01S 9/66; G01S 9/68
[52] U.S. Cl. .......................................... 367/98; 367/99; 367/151; 367/902
[58] Field of Search ................ 367/95, 105, 112, 151, 367/97–99, 13, 902; 181/400

[56] References Cited

U.S. PATENT DOCUMENTS

| | | | |
|---|---|---|---|
| 4,122,427 | 10/1978 | Karsh | 367/97 |
| 4,170,765 | 10/1979 | Austin et al. | 367/902 |
| 4,358,835 | 11/1982 | Fage | 367/151 |
| 4,380,807 | 4/1983 | Reynard | 367/97 |
| 4,464,738 | 8/1984 | Czajkowski | 367/97 |
| 4,549,286 | 10/1985 | Langeraar et al. | 367/97 |
| 4,580,251 | 4/1986 | Koukovinis | 367/151 |

FOREIGN PATENT DOCUMENTS

0077679 5/1983 Japan ..................... 367/99

Primary Examiner—Thomas H. Tarcza
Assistant Examiner—Daniel T. Pihulic
Attorney, Agent, or Firm—Charles L. Rubow

[57] ABSTRACT

A self-calibrating ultrasonic distance sensing method and apparatus are disclosed in which a transducer periodically transmits a pair of bursts of acoustic energy along an acoustic path toward a target object. Echoes of the first acoustic burst in the burst pairs from a reference target at a known distance from the transducer are used for calibration purposes, and echoes of the second acoustic bursts in the pairs are used to determine distance to the target object.

16 Claims, 7 Drawing Figures

SELF-CALIBRATING ULTRASONIC RANGE FINDER

BACKGROUND OF THE INVENTION

The invention disclosed herein relates generally to ultrasonic sensors, and more specifically to single transducer ultrasonic range finders including means for automatically compensating for the effects of variations in acoustic propagation speed on distance determinations.

It is well-known to detect the presence of and/or determine the distance to a target object by transmitting acoustic energy toward the object, receiving reflections of the transmitted acoustic energy from the object and computing distance based on the round trip travel time and the propagation speed of the acoustic energy. It is also well-known that the acoustic propagation speed varies significantly depending on parameters such as the temperature, humidity and pressure of the medium through which the acoustic energy travels.

A variety of methods and apparatus have been used to compensate for such propagation speed variations. Obviously, manual calibration can be performed by locating a reference target at a known distance from the transducer and calibrating circuitry associated with the transducer so that it indicates the correct distance. Automatic calibration schemes have also been devised in which one or more significant environmental variables are measured, and the measured values used to adjust parameters of the circuitry associated with the transducer. Yet other calibration schemes are known in which the travel time of acoustic energy from a transmitting transducer to a reference transducer at a known distance from the transmitting transducer, or to a reference target at a known distance from the transmitting transducer and back to a receiving transducer at a known distance from the reference target, is used to provide a travel time versus distance relationship which can be used in determining distance to a target object.

For example, U.S. Pat. No. 3,731,273 issued to W. Hunt on May 1, 1973 discloses a position locating system adapted for use on a plotting table in which a sound generated by electrical arcing at a probe mounted spark gap is detected at a pair of spaced capacitive transducers at fixed locations. The transit times of the sound to the transducers are determined by starting counters associated the transducers when arcing is initiated, as sensed by an inductively coupled coil, and stopping the counters upon reception of sound at the transducers. An additional spark gap at a known position relative to the transducers is provided for calibration purposes. The additional spark gap is caused to arc alternately with the probe mounted spark gap, and the resulting acoustic signals received at the transducers are converted to electrical signals which are supplied to a programmed general purpose computer.

As another example, U.S. Pat. No. 3,757,285 issued to R. Ferre on Sept. 4, 1973 discloses an acoustic range measuring device in which a main transducer alternately transmits pulse of acoustic energy and receives an echo of the pulse from an obstruction. A counter determines the number of clock pulses from a reference oscillator occurring in the time interval between transmission of an acoustic pulse and reception of its echo, the count being indicative of distance. One disclosed embodiment includes an auxiliary transducer located a known distance from the main transducer for receiving samples of the transmitted acoustic pulses. A sample and hold circuit and a voltage ramp generator are connected to initiate generation of a voltage ramp upon transmission of an acoustic pulse and terminate generation of the ramp upon receipt of the pulse by the auxiliary transducer. The final ramp voltage is used to control the reference oscillator to compensate for changes in acoustic velocity due to variations in the medium through which the acoustic energy travels.

Each of the previously described systems uses an additional transducer (spark gap in U.S. Pat. No. 3,731,273) for self-calibration, which is disadvantageous in at least some respects. Most obviously, the additional transducer adds to the cost, complexity and physical size of the system.

A somewhat simpler ultrasonic system is shown in U.S. Pat. No. 4,090,407 issued to C. Shuler, et al. on May 23, 1978 which discloses a water level measurement device comprising a tube having an open end intended to extend into the water and a sending and receiving transducer at the other end for transmitting ultrasonic signals toward the water and receiving reflections therefrom. The tube is fitted with an insert having an aperture therein, the insert being located at a known distance from the transducer. A portion of each transmitted ultrasonic signal is reflected back to the transducer from the insert. The distance between the transducer and the water surface is determined by comparison of the lengths of time required for reflections to return from the insert and the water surface. The patent, however, contains no specific disclosure of the form or spacing of the transmitted signals, how reflections from the insert and the water surface are distinguished from one another, or how the comparison is performed and water depth computed.

The applicants have devised a single transducer, pulse transmission, ultrasonic sensor employing a unique method and arrangement of components for achieving self-calibration for variations in acoustic propagation speed in the surrounding medium which overcomes certain disadvantages of prior art arrangements and provides for a relatively simple, inexpensive sensor capable of good distance sensing accuracy and operational flexibility.

SUMMARY OF THE INVENTION

The present invention is a single transducer, pulse transmission ultrasonic range finding method and apparatus which provide automatic self-compensation of indicated distance for variations in acoustic propagation speed in the medium between the transducer and target object. Apparatus according to the invention basically comprises a transducer, a reference target at a fixed distance from the transducer and transmit/receive circuitry operable to cause the transducer to periodically transmit first bursts of acoustic energy and to use electrical signals resulting from receipt of reflections of the first bursts of acoustic energy from the reference target for calibration purposes, the transmit/receive circuitry further being operable to cause the transducer to transmit periodic second bursts of acoustic energy interspersed with the first bursts of acoustic energy, and to use electrical signals resulting from receipt of the second bursts of acoustic energy from the target object to determine distance thereto. The reference target may be part of a reflector positioned to redirect acoustic energy transmitted by the transducer toward a target area and to redirect acoustic energy from objects in the target area back to the transducer.

The method of the present invention basically comprises the steps of transmitting periodic first and second interspersed bursts of acoustic energy from a transducer along an acoustic path toward a target object, providing a reference target in the acoustic path at a known distance from the transducer, and using the time required for reflections of the first bursts of acoustic energy to return to the transducer from the reference target to calibrate circuitry which determines distance between the transducer and the target object from the time required for reflections of the second bursts of acoustic energy to return to the transducer from the target object.

DESCRIPTION OF THE PREFERRED EMBODIMENT

Figure 1:
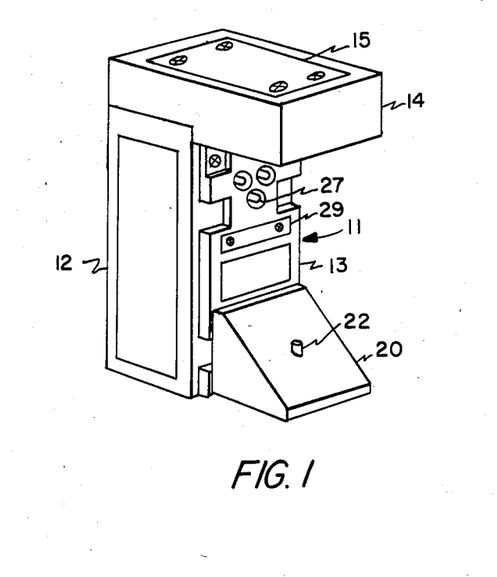
FIG. 1 is a perspective external view of an ultrasonic sensor in accordance with the present invention.

In the pictorial view of FIG. 1, reference numeral 11 generally identifies a housing for an ultrasonic sensor in accordance with the applicants' invention. Housing 11 comprises a hollow body 12 with a cover plate 13 which together form a compartment for electronic signal processing circuitry employed in the sensor. Housing 11 also includes a head 14 mounted on one end of the body, the head including a projecting portion which extends beyond the edge of the body, and a cover 15.

Figure 2:
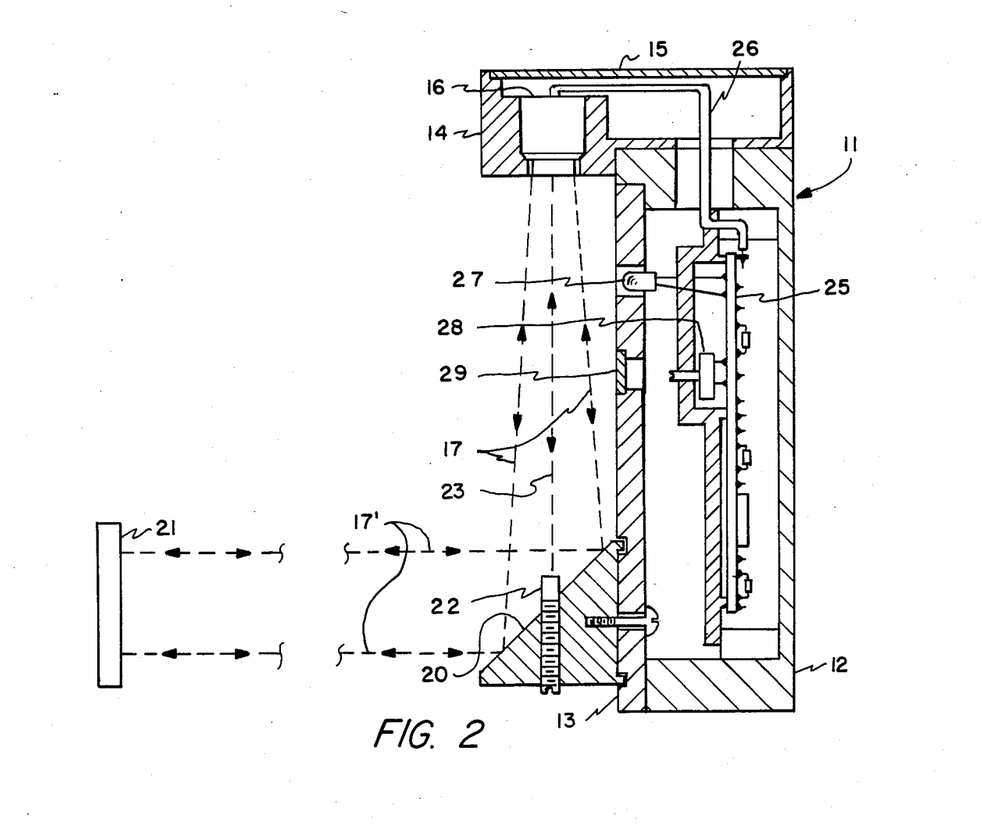
FIG. 2 is an enlarged sectional side view of the sensor of FIG. 1.

As shown on FIG. 2, an electroacoustic transducer 16 is mounted in the projecting portion of head 14, and is directed to transmit and receive acoustic energy along a path beside body 12 as indicated by dashed lines 17. A reflector 20 is mounted on cover 13 near the end of body 12 opposite the end on which head 14 is mounted. Reflector 20 is positioned to intercept and redirect acoustic energy transmitted and received by transducer 16 along a path indicated by dashed lines 17'. The path indicated by lines 17' leads to a target area in which is located a target object 21.

Reflector 20 includes a reference target 22 having a face directed toward transducer 16. As shown, reference target 22 comprises a threaded stud in the main portion of reflector 20 and extending in the direction of transducer 16. The face of reference target 22 is at a predetermined distance from the face of transducer 16. The spacing between reference target 22 and transducer 16 can be set as necessary by means of the screw threads. A portion of the acoustic energy transmitted by transducer 16 impinges on reference target 22 and is reflected therefrom back to the transducer as indicated by dashed line 23.

Reference numeral 25 identifies a printed circuit board carrying the electronic drive and signal processing circuitry for transducer 16. Such circuitry may be implemented with integrated circuit oscillators, receivers, counters and logic gates for timing the bursts of acoustic energy transmitted by transducer 16 and processing the reflections of the bursts of acoustic energy received thereby to determine distance between reflector 20 and target 21. Alternatively, the timing and signal processing may be done with a programmed microprocessor.

Circuit board 25 is shown connected to transducer 16 by means of a cable 26 and is also connected to indicator lamps, such as lamp 27, visible through holes in cover 13. Circuit board 25 is also connected to certain adjustment devices, such as device 28, to which access can be gained through a port in cover 13 under a cover plate 29.

Figure 3:
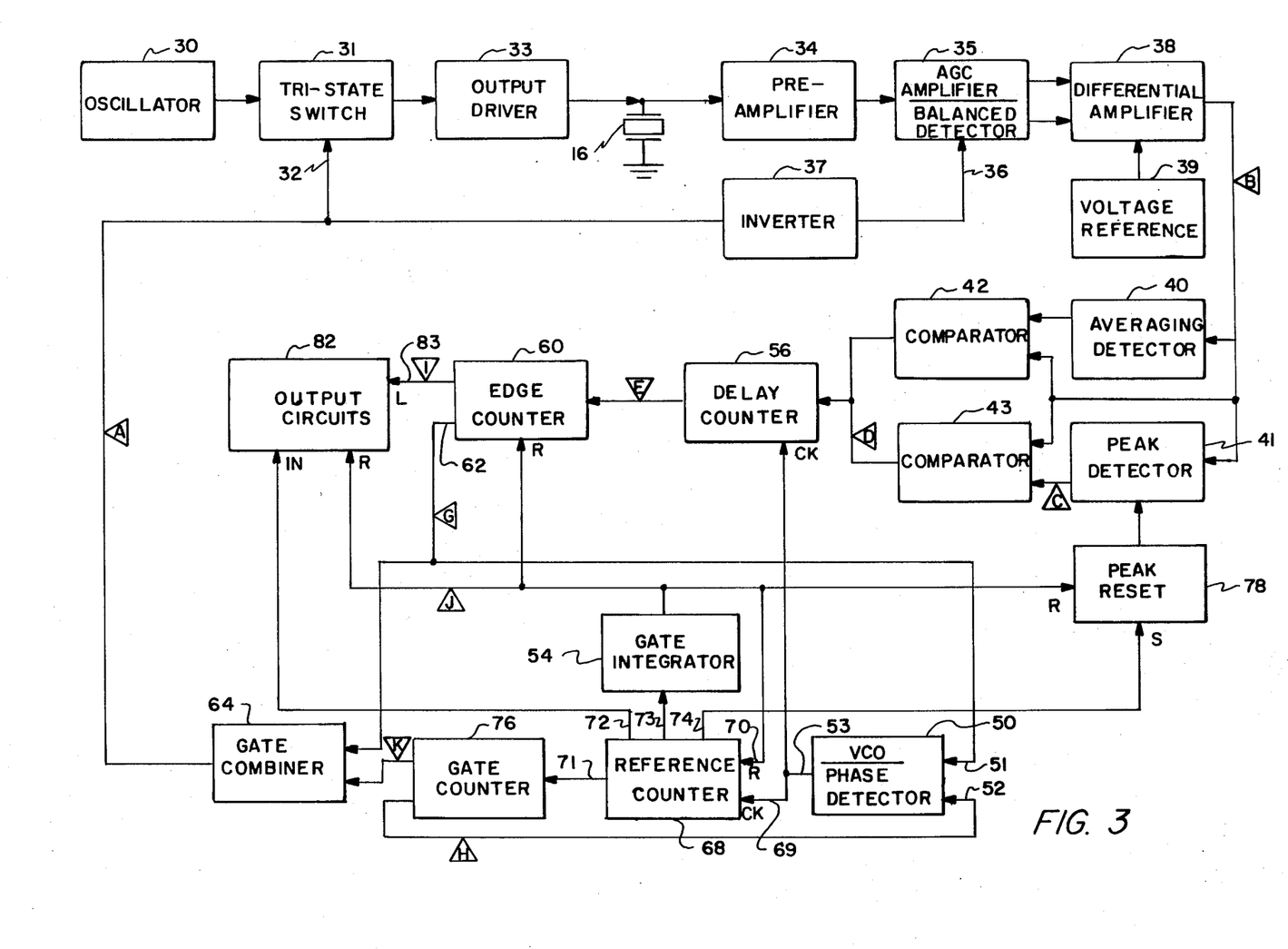
FIG. 3 is a block diagram of preferred transmit/receive circuitry for an ultrasonic sensor in accordance with the present invention.

Transmit/receive circuitry suitable for driving transducer 16 and receiving and processing signals therefrom is shown in block diagram form in FIG. 3. The general form and timing of signals at various points identified by letters enclosed in triangles in FIG. 3, and FIG. 4 discussed hereinafter, are shown in FIG. 5 where the waveforms are identified by corresponding letters.

In FIG. 3 reference numeral 30 identifies an oscillator which produces a carrier signal having a frequency chosen to correspond to the resonant frequency of transducer 16. The output signal of oscillator 30 is supplied to switching means 31 which has a control terminal 32 connected to receive a signal (first pulse in waveform A) which will be discussed hereinafter. The output signal of switching means 31 is supplied to an output driver 33 which produces the drive signal for transducer 16, the transducer being adapted to alternately transmit and receive acoustic energy.

Acoustic energy received by transducer 16 is converted into electrical signals which are supplied through a preamplifier 34 to a balanced detector 35 comprising an AM receiver whose gain is controllable by a signal at gain control terminal means 36. The signal supplied to control terminal 32 of switching means 31 is also supplied through an inverter 37 to gain control terminal means 36 so as to substantially reduce the gain of detector 35 during the intervals transducer 16 is being caused to transmit acoustic energy.

The output signals of detector 35 are supplied to differential amplifier means 38 which also receives a reference voltage from a voltage reference circuit 39. The reference voltage establishes a noise floor. If the signals produced by detector 35 exceed the level of the noise floor, amplifier means 38 passes the signals (waveform B) to an averaging detector 40 and a peak detector 41 which, in conjunction with comparators 42 and 43 respectively, perform further tests for signal validity. More specifically, comparators 42 and 43 compare the output signal of amplifier means 38 with the output signals of averaging detector 40 and peak detector 41 (waveform C) respectively.

Timing signals for the remainder of the circuitry shown in FIG. 3 originate from a voltage controlled oscillator and phase detector 50 having a pair of input terminals 51 and 52. Oscillator 50 is set to normally produce a predetermined frequency at an output terminal 53. However, the output frequency is variable depending on the relative phases of signals supplied to input terminals 51 and 52. This frequency shifting capability is utilized as will be described hereinafter to compensate for variations in acoustic propagation velocity in the environment surrounding transducer 16 due to variations in environmental parameters such as temperature, pressure and humidity.

In operation, the circuitry illustrated in FIG. 3 is initialized and reset as necessary thereafter by a gate integrator 54. Initially, a signal is supplied to control terminal 32 of switching means 31 to cause transducer 16 to transmit a burst of acoustic energy. The transmitted burst is of a predetermined duration, e.g., 50 microseconds. This initial burst of acoustic energy first impinges on reference target 22, and a portion is returned to transducer 16. Assuming that the corresponding electrical signal from transducer 16 exceeds the noise floor and passes the test provided by detector 40 and comparator 42, a delay counter 56 is enabled. Delay counter 56 receives its clock signals from oscillator 50, and is set to provide an output signal (waveform E) if the acoustic return signal has a duration at least as long as the transmitted signal. This comprises a further test to distinguish valid acoustic return signals from noise.

The output signal of delay counter 56 is supplied to an edge counter or decoder 60 having a first output terminal 62 on which is produced a pulse signal (waveform G). The output signal on terminal 62 is supplied to a gate combiner 64 which supplies a resultant pulse signal (second pulse in waveform A) to control terminal 32 of switching means 31 to cause transducer 16 to transmit a second burst of acoustic energy in a burst pair.

The signal on output terminal 62 of edge counter 60 also comprises the input signal on input terminal 51 of oscillator 50. The input signal on input terminal 52 (waveform H) is derived from a reference counter 68 having a clock terminal 69, a reset terminal 70 and a plurality of output terminals 71-74. The signal on terminal 71 is supplied to a gate counter 76 having a first output terminal connected to second input terminal 52 of oscillator 50 and a second output terminal connected to a second input terminal of gate combiner 64. Gate counter 76 supplies a signal to input terminal 52 of oscillator 50 after an interval equal to the sum of the normal round trip transit time of an acoustic signal between transducer 16 and the reference target plus the delay introduced by counter 56. The signals at input terminals 51 and 52 occur simultaneously if the oscillator is operating at the correct frequency. In the event that the signals do not occur simultaneously oscillator 50 functions to shift the frequency on output terminal 53 to bring the signals on input terminals 51 and 52 into coincidence.

Return of the echo of the first acoustic burst from the target object at a normal distance from the range finder occurs significantly after return of the echo of the second acoustic burst from the reference target. The echo of the first acoustic burst from the target object, provided it is at a higher level than the noise floor, is used to set the level in peak detector 41 whose operation is controlled by a signal from a peak reset circuit 78 which receives set and reset signals from output terminal 74 of reference counter 68 and gate intergrator 54 respectively. Return of the echo of the second acoustic burst from the target object is determined to be valid if it exceeds the noise floor level, an average level established by averaging detector 40 and a predetermined fraction of the peak level for at least the duration determined by delay counter 56. If these tests are met, delay counter 56 increments edge counter 60 which supplies a signal (waveform I) to output circuits 82 through a latch input terminal 83.

If the target object is within a normal range of distances from the range finder, the output circuits, which have accumulated a count from output terminal 72 of reference counter 68, indicate distance to the target object. However, if the target object is too close to provide for distance detection (i.e., target echoes are received within an interval shorter than twice the time required to receive both reference target echoes), output circuits 82 indicate only that a target object is present.

Since reference counter 68 is clocked by oscillator 50 whose frequency is shifted in accordance with the actual time required for acoustic energy to travel to and from the reference target whose spacing from the transducer is known, compensation is automatically provided for variations in acoustic propogation speed between the range finder and target object.

Reference counter 68 supplies a pulse signal on output terminal 73 at a time corresponding to a distance slightly greater than the maximum operating range of the range finder. This causes gate integrator 54 to produce a reset signal (first and last pulses in waveform J) which resets the range finder for a new cycle. A predetermined time interval thereafter (e.g., 50 microseconds) reference counter 68 supplies a pulse signal on output terminal 71 which causes gate counter 76 and gate combiner 64 to initiate transmission of the first acoustic burst in a new burst pair.

Figure 4A:
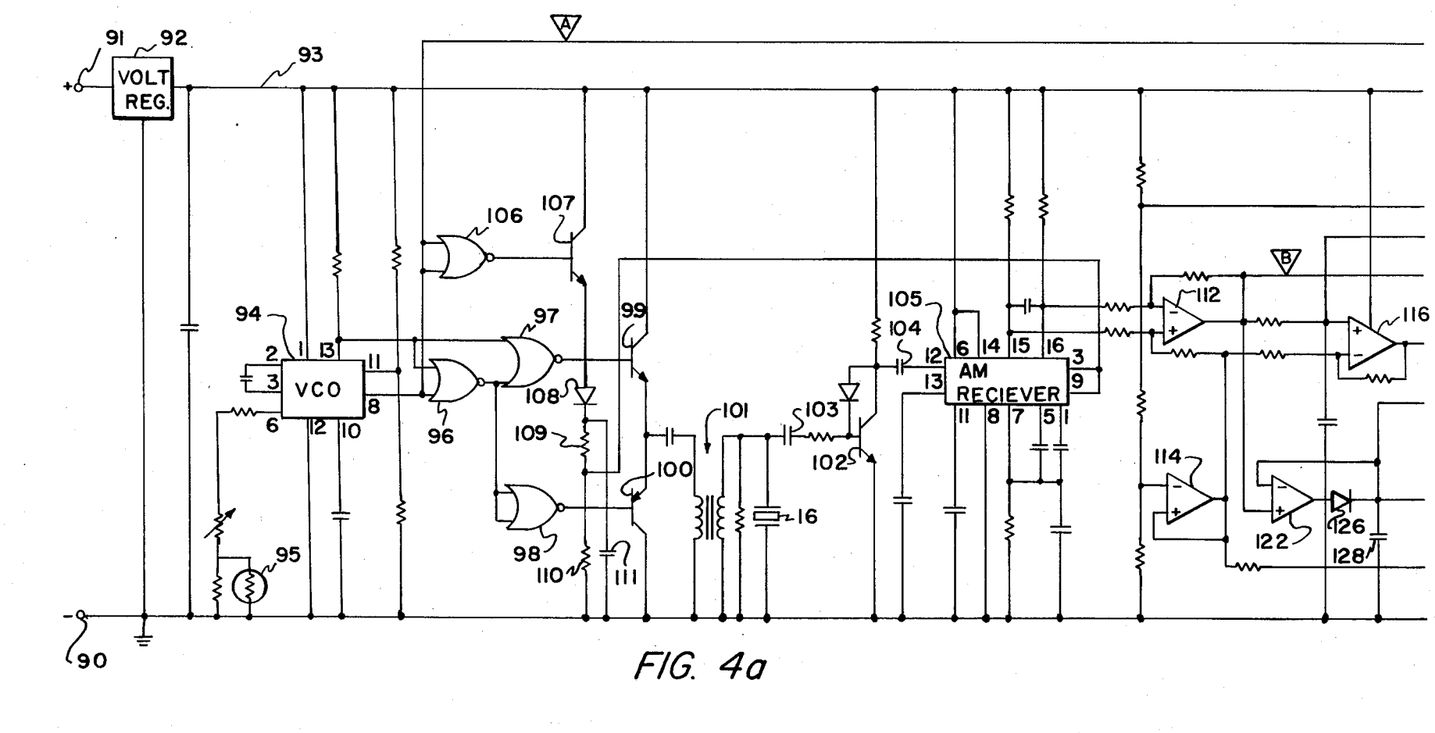
FIGS. 4a, 4b and 4c together comprise a schematic circuit diagram of transmit/receive circuitry corresponding to the block diagram of FIG. 3.
Figure 4B:
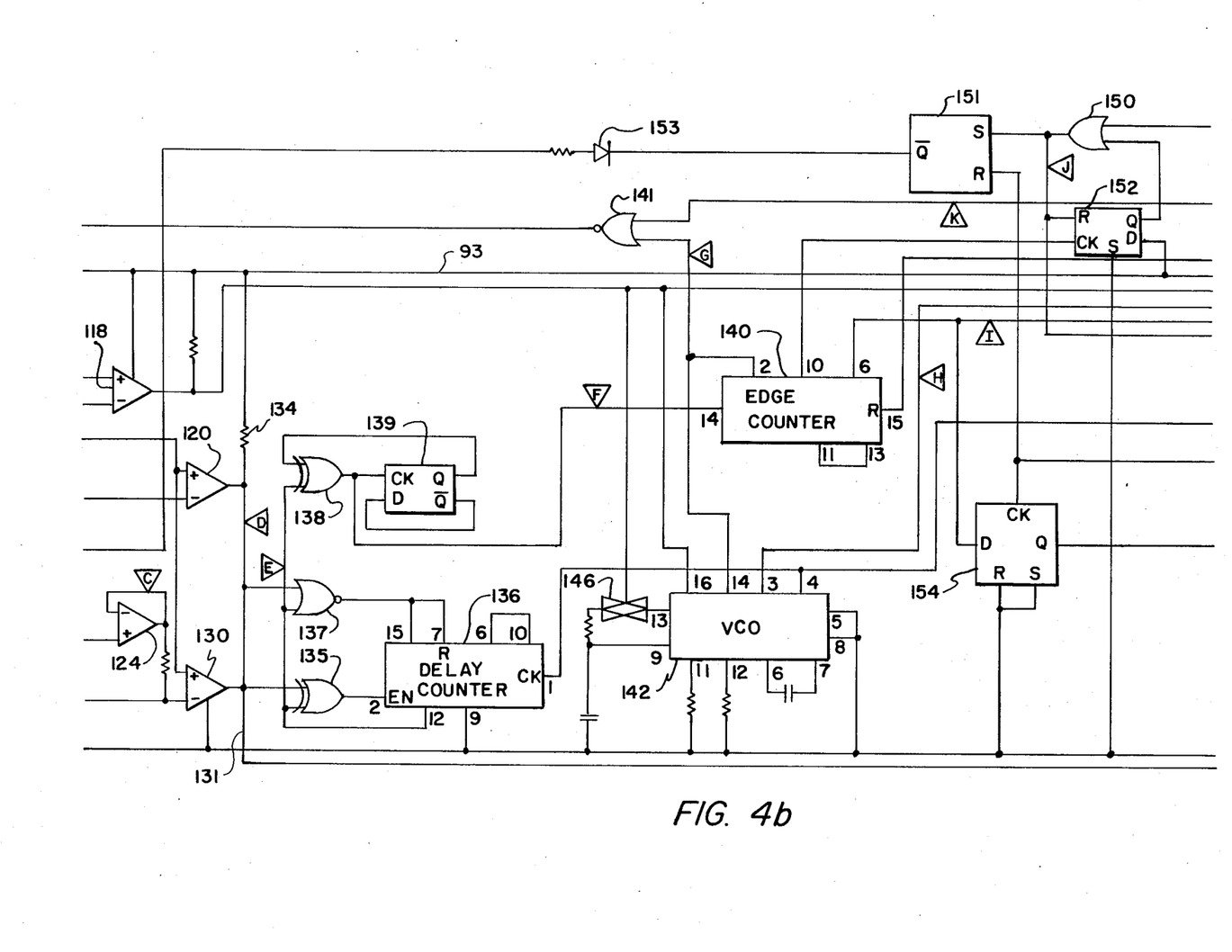
Figure 4C:
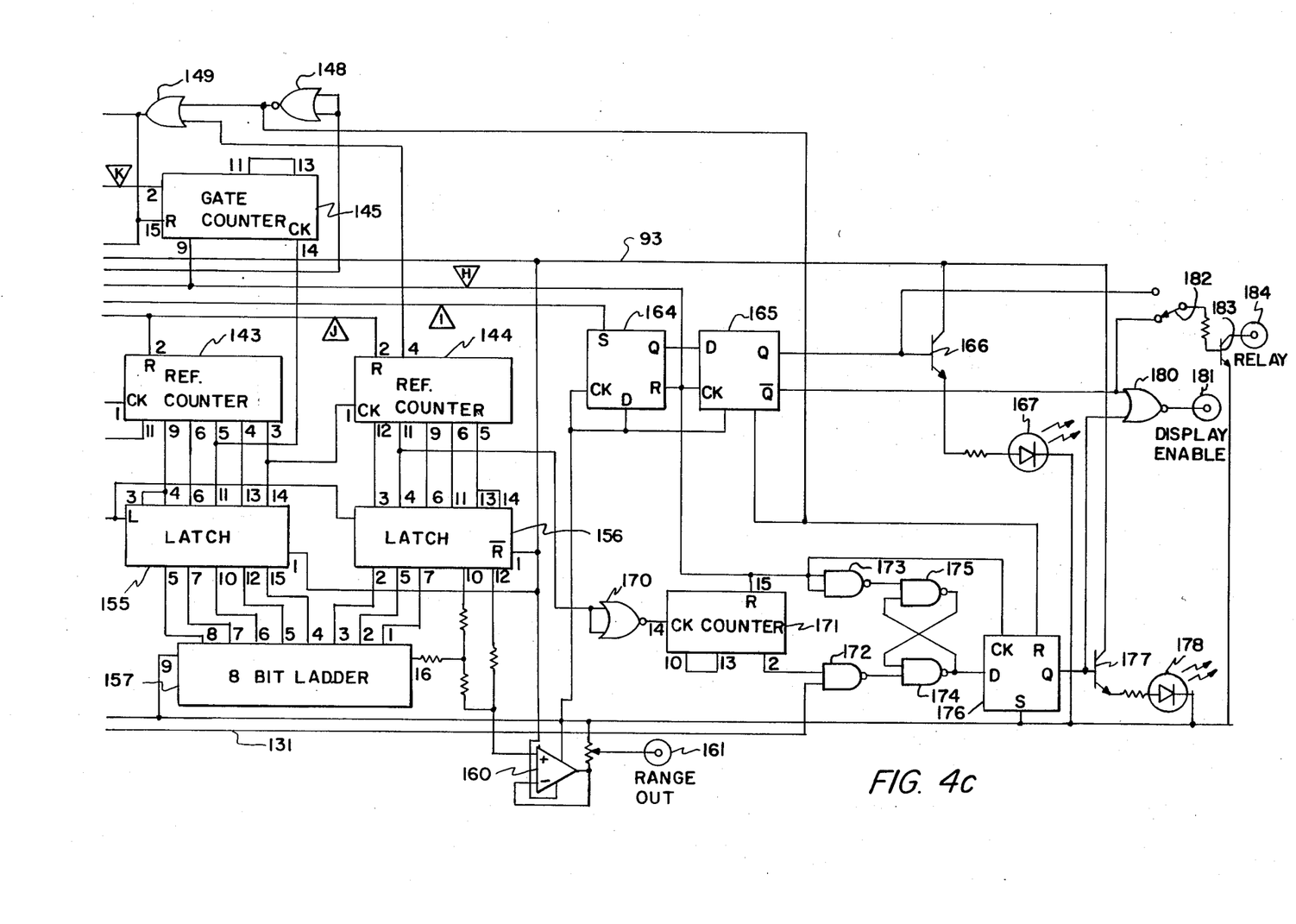
Figure 5:
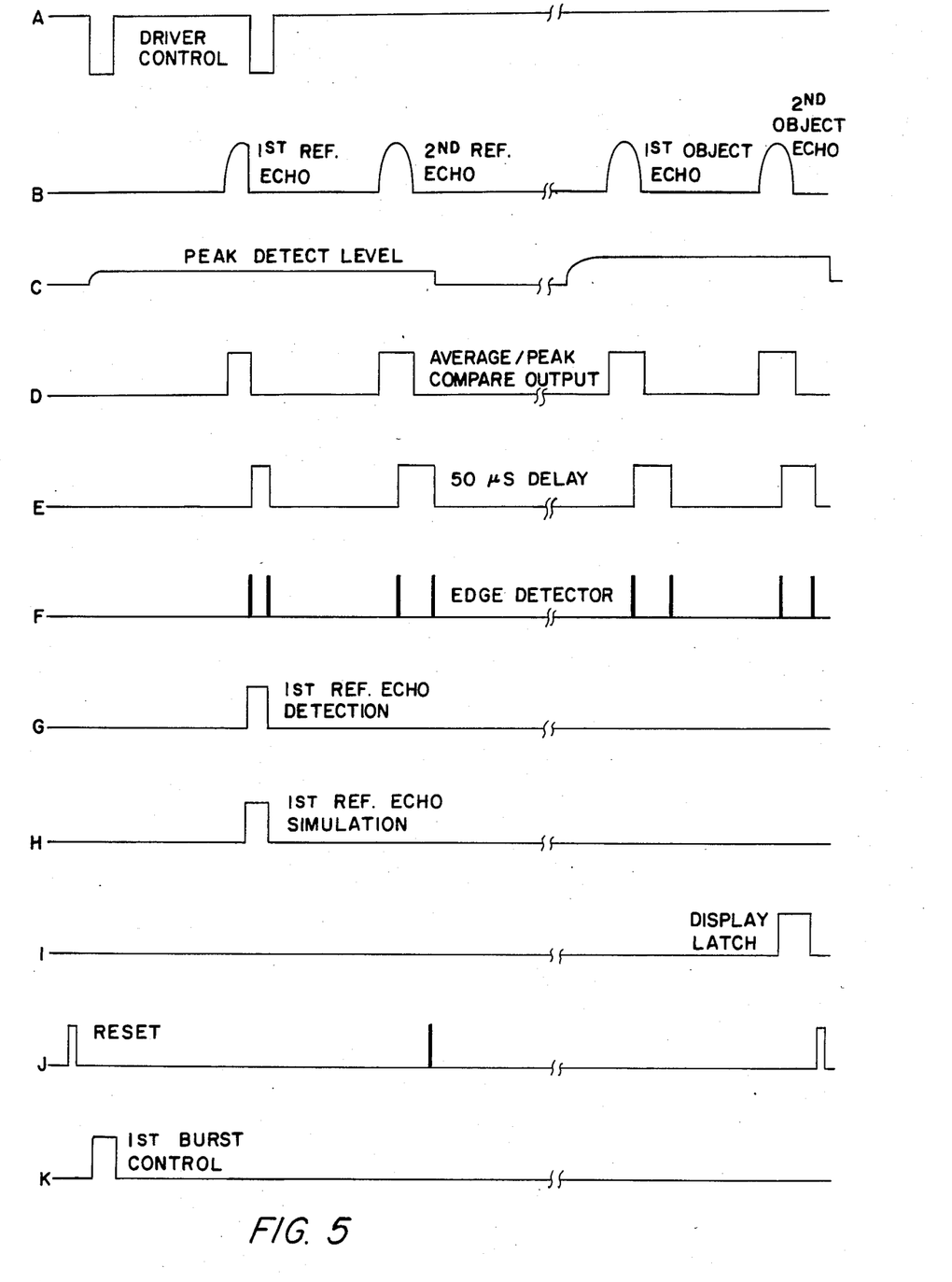
FIG. 5 illustrates the general form and timing of signals at various points in the circuit of FIGS. 3 and 4.

A specific circuit for carrying out the functions described in connection with the block diagram of FIG. 3 is shown in FIG. 4. A DC supply voltage (e.g., from 15 to 30 volts) is applied between a negative supply terminal 90 on a reference or ground bus and a positive supply terminal 91. The positive voltage is reduced to 12 volts DC by a voltage regulator 92 and supplied over a positive voltage bus 93 to other components in the transmit/receive circuitry, as required.

Reference numeral 94 identifies an integrated circuit voltage controlled oscillator whose pin 6 is connected to ground through a resistor network including a thermister or other temperature dependent resistance element 95. Oscillator 94 is set to provide a carrier frequency equal to the resonant frequency of transducer 16, which, in a specific embodiment, was nominally 220 kHz. Element 95 causes the output frequency of oscillator 94 to track the resonant frequency of transducer 16 as the resonant frequency varies with temperature. Oscillator 94 may comprise a Model XR-2207 voltage controlled oscillator commercially available from the EXAR Integrated Circuit Corporation.

Oscillator 94 produces a square wave output signal between pins 8 and 13 which are connected to a tri-state switch comprising NOR gates 96, 97 and 98. Specifically, pins 8 and 13 are connected to the input terminals of NOR gate 96 whose output terminal is connected to one input terminal of NOR gate 97 and both input terminals of NOR gate 98. A second input terminal of NOR gate 97 is connected to pin 13 of oscillator 94. The input terminal of NOR gate 96 connected to pin 8 of oscillator 94 is also connected to a gate combiner circuit which will be described in greater detail hereinafter. The gate combiner circuit produces a negative going pulse signal of predetermined pulse duration, e.g., 50 microseconds (waveform A) which enables the tri-state switch so that NOR gates 97 and 98 produce bipolar bursts of carrier frequency relative to a fixed reference.

The output signals of gates 97 and 98 are supplied to the base electrodes of a pair of complimentary driver transistors 99 and 100 respectively, which provide a drive signal to one winding of a transformer 101 through a capacitor, the other winding of the transformer producing the drive signal for transducer 16. Transducer 16 is, thus, caused to emit 50 microsecond bursts of acoustic energy spaced as will be described hereinafter.

Signals appearing across transducer 16 are supplied to the base electrode of an NPN transistor 102 through a capacitor 103. A diode is connected between the collector and base electrodes of transistor 102 which has its collector electrode connected to bus 93 through a resistor and its emitter electrode connected to ground. Transistor 102 and its associated components invert the signal produced by transducer 16 and supply the inverted signal through a capacitor 104 to pin 12 of an integrated circuit AM receiver 105, such as a Model TCA440 receiver produced by Signetics, Inc.

Receiver 105 includes an amplifier with variable gain and a balanced detector. Gain is controlled by signals supplied to pins 3 and 9 which are connected to a gain control circuit comprising a NOR gate 106, a transistor 107, a diode 108, resistors 109 and 110, and a capacitor 111. Transistor 107 is connected through its emitter and collector electrodes in series with diode 108 and resistors 109 and 110 between positive voltage bus 93 and ground. Capacitor 111 is connected in parallel with series connected resistors 109 and 110. The input terminals of NOR gate 106 are connected to pin 8 of oscillator 94. Pins 3 and 9 of receiver 105 are connected to the junction between resistors 109 and 110.

The gain control circuit operates such that it supplies a signal to receiver 105 which substantially reduces the gain of the amplifier therein during and for a short while after each drive signal burst supplied to transducer 16. The length of the period after the end of the drive signal burst during which receiver gain is reduced is determined in part by capacitor 111. This period is set sufficiently long to cover any ringing interval of transducer 16. Thus, signals transmitted by transducer 16 and caused by ringing of the transducer are prevented from being passed to circuitry following receiver 105.

The output signal from the balanced detector in receiver 105 is produced on pins 15 and 16 which are connected through resistors to the input terminals of a differential amplifier 112. The noninverting input terminal of amplifier 112 is also connected through a resistor to the output terminal of a differential amplifier 114 which produces a stable reference voltage. Amplifier 112 functions to provide a test whereby the output signal of receiver 105 is deemed valid only if its magnitude exceeds a noise floor established by amplifier 114.

The output signal of amplifier 112 is supplied through a resistor to the noninverting input terminal of a differential amplifier 116 whose inverting input terminal is connected through a resistor to the output terminal of amplifier 114. The noninverting input terminal of amplifier 116 is connected to ground through a capacitor and its output terminal is connected to its inverting input terminal through a resistor so as to form an averaging detector. The values of the resistor and capacitor connected to the noninverting input terminal of amplifier 116 are chosen to provide an averaging period at least as long as a complete operating cycle of the range finder. An average reference level signal is produced at the junction between the resistor and capacitor connected to the noninverting input terminal of amplifier 116.

The output terminal of amplifier 112 is also connected to the noninverting input terminal of a comparator 120 whose inverting input terminal is connected to the output terminal of amplifier 116. Comparator 120 produces a high output signal only if the output signal of receiver 105 passes both the noise floor and average level tests.

The junction between the resistor and capacitor at the noninverting input terminal of amplifier 116 is connected to the inverting input terminal of a comparator 118 whose noninverting input terminal is connected to a resistive voltage divider between voltage bus 93 and ground. Comparator 118 produces a high output signal except when the average signal level exceeds a noise ceiling indicative of an excessively noisy environment and system operation.

The output signal of amplifier 112 is also supplied to a peak detector comprising differential amplifiers 122 and 124, a diode 126 and a capacitor 128. Specifically, the output signal of amplifier 112 is supplied to the noninverting input terminal of amplifier 122 whose output terminal is connected through diode 126 to one plate of capacitor 128 and to the noninverting input terminal of amplifier 124. The other plate of capacitor 128 is connected to ground. The junction between diode 126 and capacitor 128 is connected to the inverting input terminal of amplifier 122. Also, the output terminal of amplifier 124 is connected to its inverting input terminal. A peak reference level signal is produced at the junction between diode 126 and capacitor 128.

The output signal of amplifier 124 is supplied through a resistor to the inverting input terminal of a comparator 130 which is also connected to amplifier 114 through a resistor. The noninverting input terminal of comparator 130 is connected to receive the output signal of amplifier 112. Comparator 130 thus compares the level of the output signal of receiver 105 with a peak reference level established by the peak detector, and produces a high output signal only if the receiver output signal level exceeds a predetermined fraction of the peak reference level.

The output terminals of comparators 120 and 130 are connected to a conductor 131 which is connected to positive voltage bus 93 through a resistor 134 whereby the conductor is biased to a positive voltage. However, comparators 120 and 130 are of a common collector configuration which effectively exhibits a grounded output when the the signal level at the noninverting input terminal is lower than that at the inverting input terminal. Thus, a positive signal (waveform D) appears on conductor 131 only if the output signals of both comparators 120 and 130 are high, indicating that a received echo has passed all of the noise floor, average level and peak level tests.

A first input terminal of an exclusive OR gate 135 is connected to conductor 131, and the output terminal of gate 135 is connected to pin 2 of an integrated circuit counter 136, such as a Model 4520 counter commercially available from Motorola, Inc. or National Semiconductor Corporation. Pin 12 of the counter is connected to a second input terminal of gate 135. A NOR gate 137 has a pair of input terminals connected to conductor 131 and pin 12 of counter 136 respectively and an output terminal connected to provide a reset signal for the counter. When so connected counter 136 effectively delays the signal supplied to pin 2 for a predetermined time period. The delay period is selected to be approximately the duration of the transmitted acoustic pulses (50 microseconds).

In the event that the signal on conductor 131 is of at least the duration established by counter 136, a delayed replica of the signal is produced on pin 12 (waveform E). This signal is supplied to one input terminal of an exclusive OR gate 138 which is interconnected with a flip-flop 139 to provide an output spike signal (waveform F) at each transition of the input signal. Thus, gate 138 and flip-flop 139 form an edge detector.

The edge detector output signal forms the clock signal for a counter or decoder 140 which produces sequential output pulse signals on pins 2 (waveform G), 10 and 6 (waveform I) in response to the clock signals. More specifically, the first clock signal produces the leading edge of a pulse on pin 2 which remains until the second clock signal. The fourth clock signal produces the leading edge of a pulse on pin 10 which remains until the fifth clock signal. The seventh clock signal produces the leading edge of a pulse on pin 6 which remains until the eighth clock signal. In the event that additional clock signals are generated during an operating cycle due to noise or multipath reflections, operation of counter 140 is stopped after the tenth clock signal by an output pulse produced on pin 11 and supplied to pin 13. Counter 140 may comprise a Model 4017 counter/decoder commercially available from Motorola, Inc. or National Semiconductor Corporation.

In operation, reflection of a first acoustic burst from reference target 22 results in a signal on pin 2 of counter 140 starting 50 microseconds after receipt of the leading edge of the reflection. The signal on pin 2 is supplied to one input terminal of a NOR gate 141 which functions as a gate combiner. The low output signal from gate 141 resulting from a pulse on pin 2 of counter 140 triggers transmission of the second acoustic energy burst in the burst pair.

Because of operation of the gain control circuit connected to pins 3 and 9 of receiver 105, transmission of the second burst cuts off reception of the reflection of the first burst (first pulse in waveform B), which is prolonged due to ringing of the transducer. Thus, the signals of waveforms D-G resulting from reflection of the first burst from the reference target are limited to 50 microseconds duration, whereas the signals resulting from the remaining reflections during an operating cycle are not subject to the same limitation.

Reference numeral 142 identifies a phase detector and voltage controlled oscillator, such as a Model CD4046 voltage controlled oscillator available from National Semiconductor Corporation. By means of connections to pins 6, 7, 11 and 12, oscillator 142 is set to produce an output pulse train on pin 4 at a predetermined nominal frequency. This pulse train forms the clock signal for delay counter 136 and for a reference counter formed of integrated circuit counters 143 and 144. In turn, counter 143 provides the clock signal for a gate counter or decoder 145.

The output frequency of oscillator 142 is, however, variable depending on the phase relationship of signals supplied to pins 3 and 14. If the leading edges of the signals supplied to these pins do not coincide a voltage is produced on pin 13. This voltage may be supplied to pin 9 through an electronic switch 146, thereby varying the oscillator output frequency. Switch 146 is controlled by the output signal of comparator 118 which establishes the noise ceiling. The output signal of comparator 118 is high as long as excessive noise is not present, thus permitting oscillator 142 to adjust its output frequency. However, if the received noise level becomes excessive, switch 146 disconnects pins 9 and 13, and the oscillator runs free at its last previous frequency.

Gate counter 145, which may comprise an integrated circuit counter similar to counter 140, receives its clock signal from pin 5 of counter 143. This clock signal is a pulse train which may have a 50 microsecond repetition rate. A pulse signal is produced on pin 9 of counter 145 at the expected time of a pulse signal on pin 2 of edge counter 140 resulting from reception of a reflection of the first acoustic burst from the reference target. The signal on pin 9 of counter 145 thus simulates the timing of the first reference echo. The output frequency of oscillator 142 varies as previously described to keep the simulated timing in agreement with the actual timing of the first reference echo. This insures that the range finder remains calibrated for correctly determining distance to a target object.

The reset signals for reference counters 143 and 144, as well as the other circuit components requiring reset signals, are produced by a NOR gate 148, OR gates 149 and 150, flip-flops 151 and 152 and a diode 153. System reset occurs either when an operating cycle is complete or when excessive noise is received.

In addition, the reference counters and peak detector are reset by the trailing edge of the edge counter output signal resulting from receipt of the second reference echo. This effectively delays operation of the reference counters for range detection purposes for a period of time equal to the round trip acoustic signal travel time between transducer 16 and reflector 20. Thus, the count accumulated by the reference counters is indicative of only the distance between the reflector on the range finder housing and the target object. With regard to peak detector operation, this reset insures that the peak reference level is set by a target object echo rather a reference target echo.

One principal input signal for the reset circuitry is provided by comparator 118 which establishes the noise ceiling. This signal is supplied to both input terminals of NOR gate 148 whose output terminal is connected to one input terminal of OR gate 149. The other input terminal of gate 149 is connected to pin 4 of reference counter 144 on which is produced a signal pulse at a time corresponding to a target object range greater than the maximum operating range of the range finder. The output terminal of gate 149 supplies the reset signals for edge counter 140 and gate counter 145, and is also connected to one input terminal of OR gate 150 which supplies the reset signal for reference counters 143 and 144.

Flip-flop 152 provides for generation of the reset signal at termination of the second reference echo. The reset terminal of flip-flop 152 is connected to the output terminal of gate 150, its Q output terminal is connected to a second input terminal of gate 150 and its clock terminal is connected to pin 10 of edge counter 140. This arrangement results in generation of a reset signal in response to the trailing edge of the output signal pulse on pin 10 of the edge counter, which pulse corresponds to the second reference echo.

The output terminal of gate 150 is connected to flip-flop 151. A high output signal from gate 150 results in a low signal at the $\overline{Q}$ output terminal of the flip-flop. This causes the voltage on capacitor 128 in the peak detector to bleed off through diode 153 and the resistor connected thereto. Accordingly, the peak detector circuit is reset to a condition in which it can establish a new peak level. Flip-flop 151 is reset by the signal on pin 11 of counter 143.

The signal on pin 11 of counter 143 also comprises a clock signal for a flip-flop 154 whose D input terminal is connected to pin 6 of edge counter 140 from which it receives a signal (waveform I) which causes a high signal at its Q output terminal upon validation of a second echo from a target object. This signal comprises a latch signal for integrated latch circuits 155 and 156 which receive the counts in reference counters 143 and 144 respectively.

The binary count in latch circuits 155 and 156 is converted to an analog signal indicative of range to the target object by means of a ladder circuit 157. The analog output signal of ladder circuit 157 is provided on pin 16 which is connected through a resistor network to the noninverting input terminal of an output amplifier 160 whose output terminal is connected to ground through a potentiometer. The wiper of the potentiometer is connected to a range output pad 161.

The output signal on pin 9 of gate counter 145 (waveform H) is supplied to a proximity latch comprising interconnected flip-flops 164 and 165. Specifically, the signal on pin 9 comprises the reset signal for flip-flop 164 and the clock signal for flip-flop 165. Receipt of a set signal by flip-flop 164 from edge counter 140 results in a high output signal at the Q output terminal of flip-flop 165. This signal forms the control signal for a transistor 166 which drives a light emitting diode 167 to indicate that a target object has been sensed.

The signal on pin 11 of reference counter 144 is supplied to both inputs of a NOR gate 170 whose output terminal is connected to the clock terminal of a counter 171 similar to counters 140 and 145. The output signal on pin 9 of gate counter 145 also comprises the reset signal for counter 171. Counter 171 defines a time window after return of the first echo from the reference target during which determination of target object range is not possible. The time window corresponds to the target object being closer to the range finder than a minimum range detection distance.

The output signal on pin 2 of counter 171 is supplied to a too close latch comprising interconnected NAND gates 172-175. Specifically, pin 2 of counter 171 is connected to one input of NAND gate 172, the other input of which is connected to conductor 131. Thus, after receipt of an echo which passes the first noise floor, average level and peak level tests, the output signal of NAND gate 172 remains low until the gate receives a signal from counter 171. During this time the latch supplies a signal to the D terminal of a flip-flop 176 which results in a high signal at the Q output terminal thereof. The signal at the Q output terminal forms the control signal for a transistor 177 which drives a light emitting diode 178. If the target object is too close for range measurement no output signal is produced on pin 2 of counter 171 and diode 178 remains illuminated.

The $\bar{Q}$ output terminal of flip-flop 165 and the Q output terminal of flip-flop 176 are connected to the input terminals of a NOR gate 180 whose output terminal is connected to a display enable pad 181. A signal is available at pad 181 only when a target object has been detected and it is sufficiently far from the range finder to permit a range measurement.

The Q and $\bar{Q}$ output terminals of flip-flop 165 are connected to terminals of a switch 182 which permits one or the other of the signals on the Q and $\bar{Q}$ output terminals to be supplied to the base of an NPN transistor 183 which produces a signal at a relay pad 184. Switch 182 permits a signal for actuating a relay to be provided either when a target object is present, or when it is absent, as desired.

In accordance with the foregoing description, the applicant has provided a single transducer, pulse transmission ultrasonic range finder which provides automatic self-compensation for variations in distance determinations due to variations in acoustic propogation velocity between the range finder and the target object. A specific embodiment has been shown and described in detail for illustrative purposes. However, a number of modifications and variations which do not depart from the applicants' contemplation and teaching will be apparent to those of ordinary skill in the relevant arts. It is not intended that coverage be limited to the disclosed embodiment, but only by the terms of the following claims:

The embodiments of the invention in which an exclusive property or right is claimed are defined as follows:

1. An ultrasonic sensor comprising:

transducer means including an electroacoustic transducer for transmitting bursts of acoustic energy in response to electrical drive pulses and converting echoes of the transmitted bursts into corresponding electrical signals;

transmit signal circuitry operable to periodically supply first and second electrical drive pulses to said electroacoustic transducer so as to cause it to transmit first and second bursts of acoustic energy, the first drive pulse being characterized to cause the first burst of acoustic energy to be of a predetermined duration, the second drive pulse being supplied in reponse to a pulse control signal;

a reference target located a predetermined distance from said electroacoustic transducer and adapted to reflect back to said electroacoustic transducer as a reference echo a portion of each burst of acoustic energy transmitted thereby;

receiver circuitry connected to receive electrical signals produced by said electroacoustic transducer, said receiver circuitry including a delay device which passes the first reference echo signal resulting from receipt of an echo of the first burst of acoustic energy from said reference target and furnishes a pulse control signal to said transmit signal circuitry only if the first reference echo signal has a duration at least as long as the predetermined duration of the first burst of acoustic energy, said receiver circuitry further including a peak detector operable to establish a peak reference level in response to a first target echo signal resulting from receipt of an echo of the first burst of acoustic energy from a target object, said receiver circuitry further including comparator means operable to pass a second target echo signal resulting from receipt of an echo of the second burst of acoustic energy from the target object if the level of the second target echo signal exceeds a predetermined fraction of the peak reference level;

oscillator means for producing periodic clock signals;

first counter means responsive to the transmission of the first burst of acoustic energy to accumulate a first count of clock signals and, upon accumulation of a predetermined first count, to produce a distance simulation signal indicative of the distance between said electroacoustic transducer and said reference target;

control terminal means on said oscillator means connected to receive the distance simulation signal and a first reference echo signal occurring at a predetermined time relative to receipt of an echo of the first burst of acoustic energy from said reference target, said oscillator means being operable to vary the frequency of the clock signals to maintain the distance simulation signal in a predetermined time relationship with the first reference echo signal;

second counter means operable to accumulate a second count of the clock signals occurring during a time interval commencing at a predetermined time relative to transmission of the second burst of acoustic energy and ending at a predetermined time relative to receipt of the second target echo provided that the second target echo signal is passed by said comparator means; and output means connected to said second counter means for producing an indication of distance to the target object based on the second count of clock signals.

2. The ultrasonic sensor of claim 1 wherein:

said receiver circuitry includes an averaging detector operable to establish an average reference level in response to the electrical signals produced by said electroacoustic transducer; and said comparator means is operable to pass the second reference echos and the first and second target echo signal to said delay device only if its level exceeds the average reference level and a predetermined fraction of the peak reference level.

3. The ultrasonic sensor of claim 2 wherein:

said oscillator means is operable to vary the frequency of the clock signals only when receiving a frequency control signal; and said receiver circuitry includes means for supplying a frequency control signal to said oscillator means only when the average reference level is less than a predetermined noise ceiling.

4. The ultrasonic sensor of claim 3 wherein:

said second counter means is further operable to produce a proximity signal when it reaches a third count indicative of a minimum target distance at which range can be measured; and latch means is provided, said latch means being responsive to the proximity signal and operable to provide an output signal indicating that the target object is too close for a range measurement until the count of clock signals advances to the third count.

5. The ulatsonic sensor of claim 4 wherein said reference target is proximate a reflector positioned to intercept at least a portion of each burst of acoustic energy transmitted by said electroacoustic transducer and redirect toward a target area, said reflector further being operable to redirect at least a portion of acoustic energy reflected from an object in the target area toward said electroacoustic transducer.

6. An ultrasonic sensor comprising:

an electroacoustic transducer adapted to transmit bursts of acoustic energy along an acoustic path in response to electrical drive pulses and to convert acoustic energy received from targets in the acoustic path to corresponding electrical echo signals;

a reference target in the acoustic path at a predetermined distance from said electroacoustic transducer, said reference target being operable to reflect back a portion of each burst of acoustic energy transmitted by said transducer; and transmit/receive circuitry operable to supply electrical drive pulses to said electroacoustic transducer for causing it to periodically transmit pairs of bursts of acoustic energy, each burst having a predetermined burst duration, and operable to receive from said electroacoustic transducer corresponding first and second reference echo signals due to echoes from said reference target and first and second target echo signals due to echoes from a target object in the acoustic path, said circuitry including variable frequency oscillator means operable to produce periodic clock signals whose frequency can be adjusted by a frequency control signal, counter means operable to count clock signals produced by said variable frequency oscillator means, said counter means being operable to produce a simulated distance signal when it reaches a first count indicative of the distance between said electroacoustic transducer and said reference target, and delay means operable to produce a first electrical signal at a predetermined time relative to the first reference echo signal provided that the first reference echo signal has a duration at least as long as the predetermined burst duration, and operable to produce second, third and fourth electrical signals if the second reference echo signal and the first and second target echo signals respectively have durations at least as long as the predetermined burst duration, said circuitry further including calibration means connected to receive the simulated distance and first electrical signals, and operable, when the simulated distance signal does not occur at a predetermined time relative to the first electrical signal, to supply a frequency control signal to said variable frequency oscillator means which adjusts the clock signal frequency so that the simulated distance signal occurs at the predetermined time relative to the first electrical signal, said circuitry further including range determination means responsive to the second target echo signal for determining distance to the target object.

7. The ultrasonic sensor of claim 6 wherein said transmit/receive circuitry includes:

a peak detector operable to establish a peak reference level based on the level of the first target echo signal; and comparator means operable to compare the level of the second target echo signal with the peak reference level and to supply a corresponding signal to said delay means only if the level of the second target echo signal exceeds a predetermined fraction of the peak reference level.

8. The ultrasonic sensor of claim 7 wherein:

said transmit/receive circuitry includes an averaging detector operable to establish an average reference level based on the average level of electrical signals produced by said electroacoustic transducer during an operating cycle; and said comparator means is operable to compare the level of the second target echo signal with the average reference level and supply said corresponding signal to said delay means only if the level of the second target echo signal exceeds the average reference level and a predetermined fraction of the peak reference level.

9. The ultrasonic sensor of claim 8 wherein:

said transmit/receive circuitry includes second comparator means operable to to prevent the supply of said frequency control signal to said variable frequency oscillator when the average reference level exceeds a noise ceiling level.

10. An ultrasonic sensor comprising:
an electroacoustic transducer adapted to transmit acoustic energy along an acoustic path in response to electrical drive signals and to convert reflections of the transmitted acoustic energy from objects in the acoustic path to corresponding electrical detection signals;
reflector means positioned to intercept at least a portion of the transmitted acoustic energy and redirect the intercepted acoustic energy toward a target area, said reflector means further being operable to redirect at least a portion of the acoustic energy reflected from an object in the target area toward said transducer, said reflector means including a reference target at a predetermined distance from said transducer for returning a portion of the transmitted acoustic energy directly to said transducer;
transmit/receive circuitry operable to supply periodic pairs of electrical drive pulses to said transducer, whereby said transducer is caused to transmit periodic first and second bursts of acoustic energy and to produce first and second reference echo signals in response to echoes from said reference target and first and second target echo signals in response to acoustic echoes from the object in the target area;
counter means which generates a first count signal upon having counted a predetermined number of clock signals commencing a fixed time interval after transmission of the first burst of acoustic energy, and generates a second signal representative of the number of clock signals which occur during the round trip travel time of the second burst of acoustic energy from said reflector means to the object and the echo thereof from the object to said reflector means;
a variable frequency oscillator adapted to supply periodic clock signals to said counter means, said variable frequency oscillator means including a phase detector having first and second input terminals and an output terminal at which is produced a voltage depending on the relative phases of signals supplied to the first and second input terminals, the frequency of the clock signals supplied by said variable frequency oscillator being controlled by a voltage supplied to a frequency control input terminal;
first connecting means connecting the output terminal of the phase detector to the frequency control input terminal; and
second connecting means for supplying the first count signal and a signal occurring the fixed time interval after production of the first reference echo signal to the first and second input terminals of the phase detector.

11. The ultrasonic sensor of claim 10 wherein said transmit/receive circuitry includes:
an averaging detector operable to establish an average reference level based on the electrical detection signals produced by said transducer during an operating cycle;
switch means in said first said connecting means operable to maintain an electrical connection between the output terminal of the phase detector and the frequency control terminal of said variable frequency oscillator when receiving a control signal; and
first comparator means operable to supply a control signal to said switch means only when the average reference level is less than a predetermined noise ceiling.

12. The ultrasonic sensor of claim 11 wherein said transmit/receive circuitry includes second comparator means operable to provide an output signal permitting determination of distance to the object only if the level of the second target echo signal is higher than the average reference level.

13. The ultrasonic sensor of claim 12 including:
a peak detector operable to establish a peak reference level based on the first target echo signal; and
said second comparator means is operable to permit a determination of distance to the object only if the level of the second target echo signal exceeds the average reference level and peak reference level.

14. A method of ultrasonically determining distance between an electroacoustic tranducer and a target object, the distance determination being compensated for variations in acoustic propagation speed in the medium between the transducer and the target object, comprising the steps of:
transmitting periodic first and second bursts of acoustic energy along an acoustic path toward the target object;
providing a reference target in the acoustic path at a fixed distance from the transducer;
establishing a noise floor;
establishing a peak reference level based on the level of the reflection of the first burst of acoustic energy from the target object;
establishing an average reference level based on the electrical signals produced by said transducer during an operating cycle;
using the time required for reflections of the first burst of acoustic energy to return to the transducer from the reference target to calibrate circuitry which determines distance between the transducer and the target object from the time required for reflections of the second burst of acoustic energy to return from the target object; and
determining distance to the target object only if the level of the reflection of the second burst of acoustic energy from the target object exceeds the noise floor and the average and peak reference levels.

15. The method of claim 14 comprising the further steps of:
counting clock signals during a time interval equal to the round trip travel time of acoustic energy to and from the target object;
counting a predetermined number of clock signal corresponding to the round trip distance between the transducer and the reference target; and
adjusting the frequency of the clock signals so that the time required to count the predetermined number of clock signals is equal to the round trip travel time required for acoustic energy to travel from the transducer to the reference target and back to the transducer.

16. The method of claim 15 comprising the further steps of:
establishing a noise ceiling; and
permitting adjustment of the clock frequency only if the average reference level is less than the noise ceiling.

* * * * *